(12) United States Patent
Miyazaki et al.

(10) Patent No.: US 9,127,245 B2
(45) Date of Patent: Sep. 8, 2015

(54) LIVING BODY HOLDING METHOD, LIVING BODY TEST METHOD, LIVING BODY GROWING METHOD, LIVING BODY HOLDING SHEET, AND LIVING BODY PROCESSING DEVICE

(75) Inventors: Takeshi Miyazaki, Yokohama (JP); Kohei Watanabe, Tokyo (JP); Toshio Tanaka, Tsu (JP); Yasuhito Shimada, Nagoya (JP); Norihiro Nishimura, Tsu (JP)

(73) Assignees: Canon Kabushiki Kaisha, Tokyo (JP); Mie University, Tsu-shi (JP)

( * ) Notice: Subject to any disclaimer, the term of this patent is extended or adjusted under 35 U.S.C. 154(b) by 769 days.

(21) Appl. No.: 12/738,045

(22) PCT Filed: Nov. 27, 2008

(86) PCT No.: PCT/JP2008/071995
§ 371 (c)(1),
(2), (4) Date: Apr. 14, 2010

(87) PCT Pub. No.: WO2009/069819
PCT Pub. Date: Jun. 4, 2009

(65) Prior Publication Data
US 2010/0221831 A1    Sep. 2, 2010

(30) Foreign Application Priority Data
Nov. 30, 2007    (JP) .................................. 2007-310946

(51) Int. Cl.
*C12M 3/00*    (2006.01)
*C12M 1/12*    (2006.01)
(Continued)

(52) U.S. Cl.
CPC ............... *C12M 21/06* (2013.01); *C12M 23/12* (2013.01); *C12M 25/01* (2013.01); *C12M 25/06* (2013.01);
(Continued)

(58) Field of Classification Search
USPC ............... 435/174, 176, 177, 180, 182, 283.1
See application file for complete search history.

(56) References Cited

U.S. PATENT DOCUMENTS 4,729,949 A * 3/1988 Weinreb et al. .................. 435/30
6,027,873 A * 2/2000 Schellenberger et al. ........ 435/4
(Continued)

FOREIGN PATENT DOCUMENTS

EP    0094193 B1 *    8/1987
JP    10-165166 A    6/1998
(Continued)

OTHER PUBLICATIONS

Supplementary European Search Report in European Application No. 08855415.9 (dated Jul. 18, 2014).
(Continued)

*Primary Examiner* — Nathan Bowers
*Assistant Examiner* — Lydia Edwards
(74) *Attorney, Agent, or Firm* — Fitzpatrick, Cella, Harper & Scinto

(57) ABSTRACT

A method of arranging a large number of living bodies, such as cells, embryos, or organisms rapidly, individually, and one by one, a holding sheet for the method, and a device for processing the living bodies. The method of holding living bodies includes using a sheet in which multiple through-holes with a size capable of holding one of the target living bodies, but not capable of holding two or more of the living bodies, are provided, to thereby arrange and hold the living bodies one by one in the multiple through-holes in the sheet together with a liquid.

14 Claims, 9 Drawing Sheets

(51) Int. Cl.
  *C12M 1/42* (2006.01)
  *C12M 1/32* (2006.01)
  *G01N 21/64* (2006.01)
  *G01N 21/03* (2006.01)
  *G01N 21/17* (2006.01)

(52) U.S. Cl.
  CPC ........... *C12M 35/08* (2013.01); *G01N 21/6456* (2013.01); *G01N 2021/0339* (2013.01); *G01N 2021/0342* (2013.01); *G01N 2021/0378* (2013.01); *G01N 2021/174* (2013.01)

(56) References Cited

U.S. PATENT DOCUMENTS

| | | |
|---|---|---|
| 7,419,820 B2 | 9/2008 | Watanabe et al. |
| 7,507,576 B2 | 3/2009 | Yamamoto et al. |
| 2005/0288721 A1* | 12/2005 | Girouard et al. ................. 607/9 |
| 2006/0057741 A1* | 3/2006 | Thompson et al. ........... 436/518 |
| 2007/0264705 A1 | 11/2007 | Dodgson et al. |
| 2008/0293138 A1 | 11/2008 | Watanabe et al. |
| 2009/0197333 A1 | 8/2009 | Saito et al. |

FOREIGN PATENT DOCUMENTS

| | | | |
|---|---|---|---|
| JP | 2002-500373 A | | 1/2002 |
| JP | 2005-214798 A | | 8/2005 |
| JP | 2005-262522 A | | 9/2005 |
| JP | 2007-504816 A | | 3/2007 |
| WO | 99/34920 A1 | | 7/1999 |
| WO | 03/035824 A1 | | 5/2003 |
| WO | WO 2005/023124 | * | 3/2005 |
| WO | 2006/106748 A1 | | 10/2006 |

OTHER PUBLICATIONS

Corrected European Search Report in European Application No. 08855415.9 (dated Aug. 19, 2014).

* cited by examiner

FIG. 1
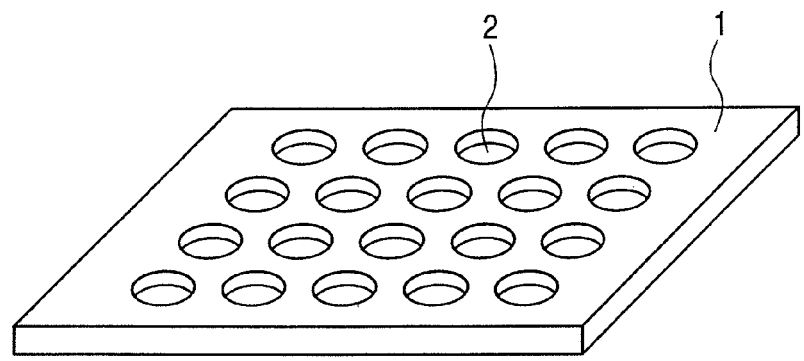
FIG. 2A
FIG. 2B
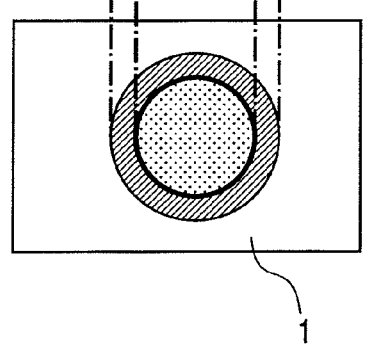

LIVING BODY HOLDING METHOD, LIVING BODY TEST METHOD, LIVING BODY GROWING METHOD, LIVING BODY HOLDING SHEET, AND LIVING BODY PROCESSING DEVICE

TECHNICAL FIELD

The present invention relates to a method of handling a living body, such as a cell, an embryo, or an individual organism, including arranging the living body to be effectively analyzed or sorted, and to a device for performing the method.

BACKGROUND ART

In recent years, the importance of handling a living body, such as a cell, an embryo, or an individual organism, to examine the function thereof and to allow a certain kind of chemical agent or physiological active agent to react with the living body to observe the function and morphological change of the living body has grown.

For example, as a sensitive, simple method of examining the effects of a chemical agent and a pharmaceutical commonly used in daily life on a living body, various tests have been attempted, such as exposing or introducing the chemical agent to cultured cells, embryos, or an individual organism, including an adult. Those tests are particularly useful for diagnosing diseases and in the field of drug development.

In the pharmaceutical field, examination of the main effect or the adverse effect of a chemical agent is essential for placing pharmaceuticals on the market. Examples of such effects on a living body include a carcinogenic/carcinostatic effect, a teratogenic effect, and an endocrine-disrupting effect.

Thus, there has been a demand for a system, which can be used to rapidly treat a large number of living bodies and to accurately evaluate the effects of the chemical agent and the physiological active agent on the living bodies by a bioassay. Also, in order to evaluate those living bodies in more detail, it is important to rapidly select and sort the living bodies.

However, in order for a large number of the living bodies to be rapidly treated using the above-mentioned system, the following predetermined operation must be effectively performed: arrangement of minute living bodies, such as embryos, at determined positions; addition of a predetermined agent to the living bodies; and measurement and sorting. In particular, an embryo must be treated in an extremely short period of time in the developmental process due to its rapid growth. However, there has not been developed a system in which the following operations are performed rapidly and practically on a large scale: arrangement of minute organisms; controlled administration of an agent, such as a chemical agent; analysis and evaluation of the living bodies with a bioassay system; and sorting of the living bodies. This results in a big obstacle to the research and development in the field.

As a method of arranging a minute living body, there is known a method in which a living body, such as a cell, is placed in a recess of a microwell plate by manipulation of a pipette or the like to isolate and arrange the living body individually. In general, because living bodies, such as cells or embryos, are very small and easily damaged, careful and accurate handling is required. For example, handling of an embryo of a biological organism requires the use of a micromanipulator. While a micropipette is manipulated or microscopic observation is performed, the position of the embryo is arranged and adjusted with optical tweezers using laser light. This operation requires skill, making it difficult to rapidly arrange and treat a large amount of embryos.

As an attempt to rapidly arrange the living bodies, Japanese Patent Application Laid-Open No. H10-165166 discloses the following method: supplying an embryo-suspending fluid to a plate for fixing cells in which a plurality of recesses, each having a shape matching a fertilized embryo, are formed on a porous plate; sucking the fluid from the back side of the plate; and arranging and fixing fertilized embryos.

In addition, Japanese Patent Application Laid-Open No. 2007-504816 discloses a device for and a method of handling cells, embryos, or oocytes.

The description of the method refers only to the method of arranging living bodies with a pipette.

Japanese Patent Application Laid-Open No. 2002-500373 discloses a method of analyzing a suspension of cells or the like while the suspension is held in a through-hole having a capillary form and a device for the method. Further, U.S. Pat. No. 6,027,873 also discloses a method of performing high-throughput screening of a suspension of cells or the like while the suspension is held in a through-hole having a capillary form.

However, while the arrangement method disclosed in Japanese Patent Application Laid-Open No. H10-165166 can be used to rapidly treat the living bodies, it has the following disadvantages: the plate for fixing cells must be a porous plate in which each recess matches the shape of a cell; and cells, such as fertilized embryos, may be damaged because the fluid is suctioned from the back side of the plate and the cells are pressed against the bottom of the plate. In addition, it is difficult to arrange a large number of living bodies using a pipette as disclosed in Japanese Patent Application Laid-Open No. 2007-504816. Besides, the methods disclosed in Japanese Patent Application Laid-Open No. 2002-500373 and U.S. Pat. No. 6,027,873 cannot arrange only one organism, such as an embryo, efficiently and cannot particularly select a specific organism for sorting and transfer purposes.

DISCLOSURE OF THE INVENTION

Hence, it is an object of the present invention to provide a method of arranging and holding a large number of living bodies, such as cells, embryos, or organisms, rapidly, individually, and one by one, as well as a living body holding sheet and a device for processing the living bodies.

Further, it is another object of the present invention to provide a method and a device, which are excellent in operability, so as to efficiently analyze or sort the living bodies that are arranged individually.

According to the present invention, there is provided a method of holding living bodies, including using a sheet in which multiple through-holes with a size capable of holding one of the target living bodies, but not capable of holding two or more of the living bodies, are provided, to thereby arrange and hold the living bodies one by one in the multiple through-holes in the sheet together with a liquid.

According to the present invention, there is provided a living body holding sheet for arranging and holding a plurality of target living bodies, comprising multiple through-holes provided in the living body holding sheet, wherein the multiple through-holes can hold the liquid that is saved in the holes and one target living body, and have a size that cannot hold two or more living bodies.

According to the present invention, there is provided a processing device that processes living bodies by using a sheet that holds the living bodies, comprising:

holding means for holding the sheet according to the present invention; and at least one means selected from the following means (A) to (G):
(A) means for arranging the living bodies in holes in the sheet;
(B) means for controlling a surrounding environment of the sheet to a given environment;
(C) supply means for supplying a liquid droplet to the holes in the sheet;
(D) observation means for observing a state of the living bodies that are held in the holes in the sheet;
(E) transfer means for transferring the living bodies that are held in the holes in the sheet from the sheet;
(F) recognition means for recognizing positions of the holes in the sheet; and
(G) means for exchanging the liquid within the holes while keeping the living bodies in the holes in the sheet.

The present invention provides a method of arranging a large number of living bodies, such as cells, embryos, or individuals rapidly and individually, a holding sheet therefor, and a device therefor. Further, the present invention provides a method and a device, which are excellent in operability, so as to efficiently analyze or easily sort the living bodies that are arranged individually. Still further, the present invention can make a physiological active agent efficiently act on the living bodies that are arranged individually. Still further, the present invention can make the living bodies grow over a long period, and can be used to easily examine the function and the morphological change.

Further features of the present invention will become apparent from the following description of exemplary embodiments with reference to the attached drawings.

BRIEF DESCRIPTION OF THE DRAWINGS

FIG. 1 is a diagram illustrating an example of a living body holding sheet;

FIGS. 2A and 2B are a cross-sectional view and a plan view schematically illustrating a condition in which living bodies are held by the living body holding sheet, respectively;

BEST MODE FOR CARRYING OUT THE INVENTION

Definition of Living Bodies

Figure 3:
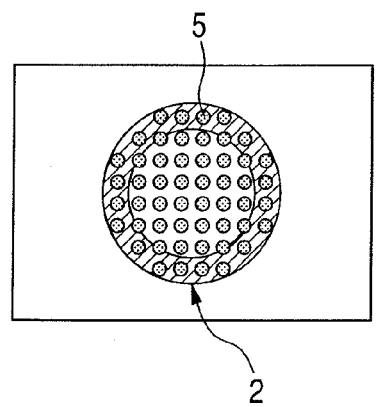
FIG. 3 is a plan view schematically illustrating a condition in which a liquid droplet is discharged from an ink jet portion so that a solution of a physiological active agent is uniformly formed on a hole portion that holds the living bodies.

A "living body" that is dealt with in the present invention includes an oocyte, an organism in an embryonic stage, an organism after hatching, an organism developing from the embryo, and an egg cell. The organisms include all stages at which a vertebrate grows from a fertilized embryo to an adult. Further, an embryo is an organism that is at a stage from embryo fertilization until hatching. Hence, the embryo (fertilized embryo) can be preferably used as the organism in an embryonic stage. Further, the organism developing from the embryo includes, for example, an organism whose embryo is in the stage from fertilization until hatching, or even after hatching, from fertilization until the organism has become a juvenile fish (regarded as an adult) in the case of fishes, or has become larva in the case of amphibians.

As the vertebrate, a large animal, such as a pig, a dog, a monkey, or a human, may be used in addition to a small animal, such as a rat or a mouse. Amphibians or fish that are prolific are preferred. In view of the maintenance of testing facilities, it is preferred that fish that are as small and as prolific fishes as possible be used. Further, the fish embryo is preferably transparent. Besides, in order to compare the effect of a chemical agent on fish with the effect of the chemical agent on humans, it is preferred to use amphibians or fish whose genomic sequences are disclosed or are going to be disclosed in the near future. Particularly preferable examples of such amphibians or fish include xenopus, Japanese putter fish, killifish, and Zebrafish.

Living Body Holding Sheet

Hereinafter, a living body holding sheet used in the present invention will described in detail. An example of the living body holding sheet according to the present invention is illustrated in FIG. 1. The living body holding sheet has multiple through-holes (openings) 2 in a base 1. Each of the holes is of a size that can hold one living body, but cannot hold two living bodies. Further, it is desirable to design the living body holding sheet so that the living body and a liquid can be held thereby. It is presumed that the liquid is held by an inner wall of the hole in the living body holding sheet due to the interaction force (adhesion force) of the liquid, and the living body is held by the surface tension of the liquid in a state in which the living body is surrounded by the liquid. Hence, it is preferred that the living body holding sheet hold liquid that includes one living body within each of the holes, and that each of the holes be of a size that can hold one living body together with the liquid that is held within the hole, but cannot hold two or more living bodies. In other words, it is preferred that each of the holes be of a size that can hold the liquid, which includes one living body, but cannot hold the liquid, which includes two or more living bodies. As one example, FIGS. 2A and 2B illustrate a cross-sectional view and a plan view of a condition pattern in which a living body 3 is held within the hole together with liquid 4 when the living body is substantially spherical, and the hole 2 is circular, respectively.

The base can be made of any materials in which the holes can be formed. For example, the following can be used: metals, such as iron, copper, and aluminum and alloys containing them; ceramics made of glass, alumina, silicon and the like; and plastic resins made of teflon, polyethylene, polypropylene, polyester, polyacetal, silicon rubber, polycarbonate, polyvinyl chloride, polystyrene, nylon, and the like and complex materials thereof. However, it is preferred that the material of the base be basically not soluble in water and the component of the material not be eluted. Further, the inner walls of the holes in the living body holding sheet can be subjected to a hydrophilic treatment or a roughening treatment so as to readily hold a liquid. The color of a material of a living body holding sheet surface is not particularly restricted, but it is preferred that the living body holding sheet surface be made of a material that suppresses reflection of light for microscope observation and a material having no self-fluorescence for fluorescence microscope observation.

In the present invention, each of the through-holes 2 is required to have an appropriate opening area according to the size of the living bodies and is also required to have an appropriate thickness. That means, the inventors have found that efficiently and stability of holding one living body in each of the holes is significantly affected by the size (dimensions) of the holes, which is the opening area and the thickness.

Further, a configuration of each of the holes, which is exemplified in FIG. 1 is circular, but can be of any configuration including a polygon, such as a quadrangle, an oval, or have a star shape. However, the opening area of each of the holes is an important parameter for efficiency and stability in holding one living body in the hole.

The sheet of the present invention has a finite thickness. Therefore, the configuration of each of the holes actually has a structure of a cylinder in which the hole penetrates from a front surface to a rear surface while keeping the configuration thereof. In this case, the holes penetrate in a direction perpendicular to the plane of the sheet. That is, the configuration of each of the holes can be of a columnar structure in the case of a circle, and a quadrangular prism structure in the case of a quadrangle.

It is preferred that the opening area of each hole be in a range of from 1.05 times to 3.61 times the maximum cross-section of the target living bodies. Also, in order to further increase the probability of holding the living bodies in the holes one by one and hold the living bodies in the holes with even more stability, it is more preferred that the opening area of one hole be in a range of from 1.2 times to 2.25 times the maximum cross-section of the living body. The maximum cross-section of the living body corresponds to a cut surface that passes through the center of gravity of a sphere when the living body is the sphere or a substantially spherical body, such as an embryo. Further, when the living body is a juvenile fish or larva of amphibians, the opening area of one hole can be obtained with respect to its postural balance that can be stably taken in the holes that hold the liquid. For example, in a case of an embryo cell having a diameter of about 1 mm and a maximum cross-section of $0.79 \text{ mm}^2$, it is preferred that the circle-shaped opening area of the hole be in a range of from $0.87 \text{ mm}^2$ to $2.83 \text{ mm}^2$. Further, it is preferred that the living body holding sheet be normally kept in a horizontal position when the living body is held.

Further, the size of the holes that cannot hold two or more living bodies is indicative of a size that cannot accommodate at least two maximum cross-sections of the living bodies in a geometrical arrangement.

When the opening area of each the holes is smaller than 1.2 times of the maximum cross-section of the living body, it is difficult to arrange the living body in the hole. When the opening area is larger than 2.25 times thereof, multiple living bodies would be frequently arranged in each of the holes. Further, the holes having multiple different sizes may be provided in the same base.

The thickness of the base material need not be particularly uniform. However, it is desirable that the thickness of the base material, which is in the vicinity of the holes, be 0.2 times to 1.9 times the maximum thickness of the target living bodies for the purpose of arranging only one living body particle in each of the holes. The maximum thickness of the living bodies is indicative of the diameter of the maximum cross-section when the living bodies are spheres or substantially spherical bodies, such as embryos. Further, when the living bodies are juvenile fishes or the larva of the amphibians, the thickness can be obtained with respect to the balance that can be stably taken in the holes in the living body holding sheet, which actually hold the liquid. As an example, when the embryo having a diameter of about 1 mm is held, it is preferred that the thickness of the holes be in a range of from 0.2 mm to 1.9 mm. When the thickness of the holes is smaller than 0.2 times the maximum thickness (diameter in the case of a sphere) of the living body, the living bodies cannot be stably held because the retaining amount of liquid is small with respect to the organism. As a result, a rate at which the living bodies fall out when they are arranged increases. Further, when the thickness of the holes is larger than 1.9 times the maximum thickness (diameter in the case of a sphere) of the living body, a rate at which multiple living bodies are held increases, and the purpose of arranging only one living body particle in each of the holes cannot be achieved.

Further, when the thickness of the base material in the vicinity of the holes is set to be equal to or smaller than 1.0 times of the maximum thickness of the living bodies, the living bodies can adequately be arranged in the centers of the holes. As a result, the centers of the living bodies in the respective holes can be arranged on one plane. Thus, in obtaining an image by means of an array sensor, such as a CCD, focal depth can be adjusted with respect to the multiple living bodies, and hence focus can be achieved for multiple living bodies at the same time.

Further, the living body holding sheet 1 has multiple through-holes 2 in the base 1. Although the holes 2 can be arranged in any regions, it is preferred that the holes 2 be regularly arranged from the viewpoint of automation. Further, the number of holes that are provided in a base 1 or the arrangement density is not limited. However, from the viewpoint of operability, the arrangement density is preferably in a range of from 5 holes/$\text{cm}^2$ to 70 holes/$\text{cm}^2$, and more preferably in a range of from 10 holes/$\text{cm}^2$ to 40 holes/$\text{cm}^2$ when the diameter of the holes is about 1 mm. That is, when the arrangement density is smaller than 5 holes/$\text{cm}^2$, an area covered by portions other than the holes increases, and a liquid droplet is liable to be isolated in that area. Accordingly, the living bodies are arranged in the region other than the holes together with the liquid droplet, resulting in a reduction of the efficiency of the arrangement. Conversely, when the arrangement density is greater than 70 holes/$\text{cm}^2$, a distance between adjacent holes is not sufficiently large, and hence drawbacks, such a as contamination, can easily occur in the subsequent handling in which the liquid that holds the organism mixes with liquid that is held by the adjacent hole.

That is, it is desirable that an area ratio (opening ratio) of the holes with respect to the living body holding sheet be in a range of from 7.9% to 70%.

Further, according to the present invention, it is preferred that the living bodies be held one by one in the multiple holes in the living body holding sheet, but it is not always necessary for all of the holes in the sheet to hold the living bodies. However, when a rate at which the living bodies are held in the holes is extremely low, the efficiency is reduced when the living bodies are examined at a later point in time.

The living body holding sheet according to the present invention is characterized by the through-holes, and has the following advantages as compared with the conventional bottomed well:
  i) ease of arrangement of the living bodies;
  ii) ease of removal of the living bodies;
  iii) the growth of the living bodies is not affected by the impulse from the bottom plate, because the living bodies are out of contact with the bottom plate;
  iv) the gas exchange is liable to be conducted, because the area of the liquid within the holes, which comes in contact with the external air, is large; and
  v) there is no noise factor in an observing process, such as reflected light, or self fluorescence from the bottom plate, because a bottom plate is absent.

Method of Holding Living Body

With the use of the living body holding sheet according to the present invention, the living body, such as an embryo, can be easily arranged. More specifically, an embryo can be easily arranged in each of the holes together with the liquid one by one, because the liquid in which the living body is dispersed is brought into contact with the living body holding sheet. A method of holding living bodies is to arrange and hold the living bodies one by one in the multiple through-holes in the sheet together with a liquid, including using a sheet in which multiple through-holes with a size capable of holding one of the target living bodies, but not capable of holding two or more of the living bodies, are provided.

The significant feature of the present invention resides in that only one living body is held in each of the through-holes together with the co-existing liquid. The feature of the present invention is clearly distinct from the known conventional art in which a protrusion is formed in the interior of the through-hole so that a partial cross-section of the hole is smaller than the living body size, or the living body is supported by the structure combined with the bottom plate.

The liquid containing the living bodies can be contacted with the living body holding sheet using any method, such as a method of pouring the liquid containing the living bodies into the sheet from above, or a method of immersing the sheet into the liquid containing the living bodies. As one of methods of pouring the liquid containing the living bodies from above, a known slit coater may be used, so that the liquid containing the living bodies can be uniformly applied to the entire surface of the sheet from a slit die. Further, excess liquid that contains the living bodies after having been brought into contact with the sheet can be easily removed by inclining the sheet, wiping off the rear surface of the sheet with a blade, or spraying the sheet with air. When the sheet is sprayed with air, it is necessary to control the air pressure or the spray angle so as not to dislodge the living bodies that are held in the holes. Further, when the excess liquid connects multiple hole portions, contamination is liable to occur between the holes.

Further, the living bodies are liable to be held in a portion other than the hole portions. For that reason, it is preferred that the liquid droplet not remain in the portion other than the hole portions to the maximum extent possible. A suspension in which a large number of fish embryos are suspended in water is an example of a liquid that contains the living bodies.

It is preferred that at least one surface of the living body holding sheet be a hydrophobic surface. When at least one surface of the sheet is a hydrophobic surface, it is possible to easily remove the excess liquid, because the aqueous liquid is repelled in a region other than the holes. In that case, a contact angle of the hydrophobic surface with respect to the liquid needs to be equal to or larger than about 90 degrees.

In order to hold the living bodies in the living body holding sheet by the surface tension of liquid, liquid having the surface tension of about 25 mN/m or higher is preferred. When the surface tension is lower than 25 mN/m, it is difficult for the living bodies to be held within the holes together with the liquid, and the living bodies frequently fall out due to slight vibrations. The liquid that is held by the sheet together with the living bodies is preferably an aqueous liquid that is high in affinity for the living bodies and liable to adhere to the inner walls of the holes.

Examples of an aqueous liquid include water, alcohol, glycol solvent, or glycerin, and an aqueous solution including those aqueous liquids. The water content in the aqueous solution is preferably 50% or more. Further, for the purpose of preventing the evaporation of the liquid that holds the living bodies from the sheet, or for the purpose of stabilizing the holding of the living bodies, at least any one of a moisturizing agent, a surface tension adjuster, and a thickener can be added to the aqueous solution.

Examples of the moisturizing agent as the additive include polyhydric alcohols, such as glycerin, propylene glycol, butylene glycol, and sorbitol; mucopolysaccharides, such as hyaluronic acid and chondroitin sulfate; and protein hydrolysates, such as soluble collagen, elastin, and keratin. Each of them can be used singly or a plurality of them can be used in a mixture.

As the surface tension adjuster, one kind or a plurality of kinds of the following surfactants may be added: a soluble anionic surfactant, a soluble cationic surfactant, a soluble amphoteric surfactant, and a soluble nonionic surfactant. It should be noted that the addition amount that does not make the surface tension of liquid less than 25 mN/m is preferred.

As the thickener, exemplified are soluble polymeric compounds including: starches, such as a starch modified by oxidization, a starch modified with an enzyme, a starch modified by thermochemistry, a cationic starch, an amphoteric starch, or an etherified starch, or the compounds including soluble polymeric compounds, which comprise cellulose derivatives, such as carboxy-methylcellulose, hydroxyethylcellulose, or ethylcellulose; natural or semisynthetic polymers, such as casein, gelatin, or soya bean protein; or polyvinyl alcohols, such as a completely or partially saponified polyvinyl alcohol, an acetoacetylated polyvinyl alcohol, a carboxy-modified polyvinyl alcohol, an olefin-modified polyvinyl alcohol, or a silyl-modified polyvinyl alcohol. At least one of those soluble polymeric compounds may be suitably selected and used.

In the present invention, a preferred viscosity of the liquid to be used is equal to or larger than 0.1 Pa·s (Pascal seconds), and the thickener can be added as occasion demands.

Further, when it is necessary to control the salt concentration or the pH to be suitable for the living bodies, a salt, such as sodium chloride, or a diverse pH adjuster, or a preservative or an antimicrobial can be appropriately added to the liquid.

Administration of Material

In a method of the present invention, after the living bodies have been held by the living body holding sheet, a test having a process of administering a material to the respective living bodies that are held by the sheet and testing a correlation with the material can be further conducted.

The process of administering the material to the living bodies that are held in the holes in the living body holding sheet together with the liquid and examining its action is described in more detail below.

The material that is administered to the living bodies is not particularly limited, but includes an organic or inorganic chemical material, a metal, a chemical compound thereof, a compound material of the living bodies, a physiological active agent derived from the living bodies, deoxyribonucleic acid (DNA), bacteria, a virus, a complex with those chemical materials, or the mixture of the multiple chemical materials. It is preferred to administer liquid including one or multiple kinds of materials to the holes in the living body holding sheet.

In the present invention, it is possible to examine whether the material that has been administered to the living bodies acts. Further, when the material acts, it is possible to examine a change in the action with respect to a change in the administered quantity or a change in the action with time. There can be preferably used a method of dissolving or dispersing the material in the solvent, such as water or an organic solvent, and administering the material as a liquid. The above-mentioned liquid is discharged as a liquid droplet to thereby enable the liquid to be directly administered to the living bodies that are held in the holes in the living body holding sheet. As a device that discharges the liquid as a liquid droplet, there can be preferably used a micropipette, a microdispenser, or a device that discharges the liquid droplets from a nozzle by means of an energy generating element, that is, a discharge device using an ink jet method. The discharge device using the ink jet method is preferably used, because minute liquid droplets can be discharged. Further, among the ink jet methods, a thermal ink jet method and a piezoelectric ink jet method are preferably used.

In the present invention, it is preferred to administer the liquid as liquid droplets, each of which has a volume of 100 pl (picoliter) or less. That is, there is a risk that the minute living bodies that are held in the holes in the living body holding sheet together with the liquid droplets would fall out due to the discharge pressure of the liquid droplets when the liquid droplet is larger than 100 pl in volume. Further, it is preferred to disperse and drop the minute liquid droplets over the entire area of the holes in order to prevent the liquid droplets from being locally administered to the living bodies. In that case, it is desirable that 100 or more liquid droplets be dispersed and administered with respect to one hole. With such an operation, the material can act with a high level of reproduction on the living bodies within the area. The proper administered liquid droplet position is schematically illustrated in FIG. 3. FIG. 3 is a schematic plan view illustrating the living body holding sheet and represents an impact position 5 of the liquid droplet in the hole 2.

Liquid Exchange

In the present invention, the liquid within the holes that holds the living bodies can be exchanged for the purpose of controlling the action period of the material that is administered to the living bodies or for the purpose of removing a material that is secreted from the living bodies.

In that case, it is necessary to conduct a liquid exchange smoothly so that the living bodies that are held in the holes do not drop out of the holes. In order to conduct the liquid exchange smoothly, it is preferred to provide a liquid exchange portion that communicates with the holes for holding the living bodies in the living body holding sheet.

Figure 14A:
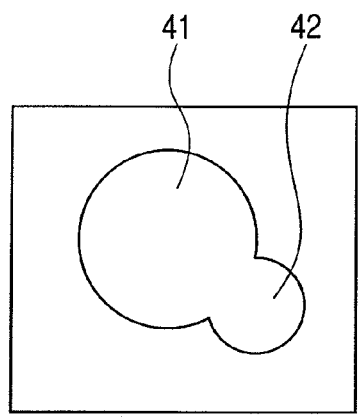
FIGS. 14A and 14B are enlarged diagrams, each illustrating a living body holding sheet with a solution exchange portion.
Figure 14B:
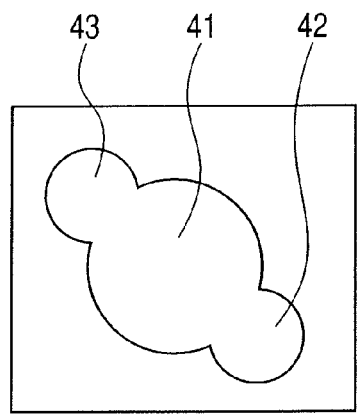

An example of the living body holding sheet having the liquid exchange portion is illustrated in FIGS. 14A and 14B.

Referring to FIG. 14A, there is provided a liquid exchange portion 42 that communicates with a through-hole 41, which can hold one living body. Further, as illustrated in FIG. 14B, multiple liquid exchange portions 42 and 43 that communicate with the hole can be provided in order to conduct the liquid exchange more efficiently. It is preferred that the liquid exchange portion be a hole that is smaller in area than the hole 41 that holds the living body. That is, when the liquid exchange portion has an area that is equal to or larger than the hole 41 that holds the living body, the possibility that the living body is arranged in the liquid exchange portion is high, with the result that the intended liquid exchange becomes difficult. Further, the liquid exchange portion may not be formed of the through-hole, but can be formed of a bottomed well. In any cases, it is necessary that the liquid freely flow between the through-hole 41 that can hold the living body and the liquid exchange portion. As a method of more smoothly exchanging the liquid, one specific example is described below. In FIG. 14B, when the liquid is sucked from the liquid exchange portion 43 simultaneously when the liquid to be exchanged drops in the liquid exchange portion 42, the liquid exchange can be smoothly conducted without any large fluctuations of the liquid amount. Further, in both of FIGS. 14A and 14B, it is possible for a tube or a thin line to be connected to the liquid exchange portion 42 to naturally discharge the excess liquid downward.

Observation of Living Body

In the present invention, an observing means is a means for capturing the state and change of the living body as an image. More specifically, a visible light is applied to the living body that is held by the living body holding sheet so as to observe the configuration of the living body by imaging means. As the imaging means, a camera or a CCD can be used. Further, a lens system is disposed between an imaging portion and the living body to enlarge the living body so as to observe the details of the living body.

Further, in the present invention, there can be provided a means for observing fluorescence from the living body. Fluorescence observing means applies an excitation light to the living body that is held in the living body holding sheet from an excitation light source and observes the luminous living body by the imaging means. The fluorescence imaging means can be formed of a scanner, as well as the camera and the CCD. When the living body is imaged in a state where the excitation light is applied to the living body to make the interior of the living body luminous, the luminous portion can be readily detected. Further, a bright field image obtained by applying the visible light and a fluorescence image obtained by applying the excitation light are combined together by an image processing means, to thereby enable to the living body to be observed in more detail.

Growth of Living Body

In the present invention, the living body can grow within the hole in the living body holding sheet. Hence, the present invention includes a growing method using multiple living bodies, which method includes a process of making the living bodies grow within the holes in the living body holding sheet after the living bodies are held by the living body holding sheet. Further, it is preferred to administer a material (for example, nutritional material for maintaining the survival of the living bodies) to the respective living bodies for growing in the growing process. In the growing method, an embryo can grow, and hatching is enabled.

In order to conduct the growth of the living bodies for a long period of time, it is important to control the proximity of the sheet that holds the living bodies to a given environment. That is, it is preferred to adjust the temperature to a temperature suitable for the maintenance and growth of the respective living bodies.

For example, in the growth of a Zebrafish embryo, it is necessary to control the surrounding temperature so that the interior of the holes in the living body holding sheet is kept at 25° C. to 30° C.

Further, in the growth of the living bodies, it is important to suppress the evaporation of the liquid within the holes in the living body holding sheet as much as possible. Accordingly, the relative humidity of the hole periphery is maintained at 60% or higher, and more preferably at 80% or higher.

Further, for the purpose of maintaining and growing the living bodies, a living body maintaining material, such as water, can be administered to the interior of the holes in the living body holding sheet by the above-mentioned administering means. Further, in the growing process, a chemical material or a living body maintaining material can be additionally administered by a method using evaporation, spray, mist, micropipetting, or an ink jet discharge device.

Transfer of Living Body from Holes

In the present invention, a significant feature of the living body holding sheet resides in that the living bodies can be easily transferred to another container from the holes of a specific living body holding sheet, because the living bodies are held in the through-holes that are larger in size than the living bodies.

That is, the holes in the living body holding sheet are different from the conventional bottomed well in that the living bodies that are held in the through-holes can be readily taken out using any operation, such as using a pipette. As a means for taking out the living bodies, a force is exerted on the interior from one opening of the holes in which the living bodies to be taken out are arranged, and the living bodies are taken out of an opposed opening side.

Figure 5A:
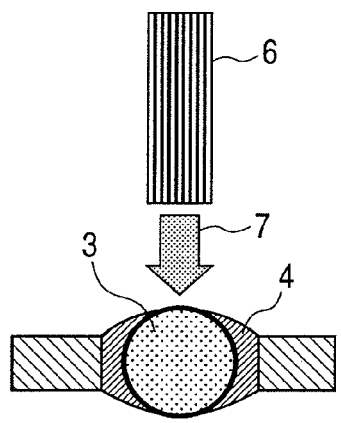
FIGS. 5A and 5B are cross-sectional views, each illustrating an example of a condition in which the living bodies are transferred to another container by spraying the living bodies with air from the interior of the hole of a specific living body holding sheet.
Figure 5B:
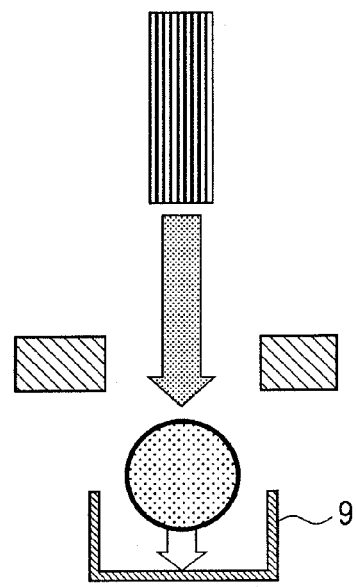
Figure 6A:
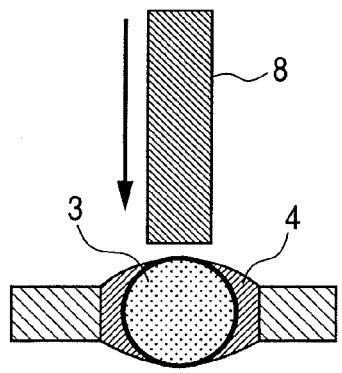
FIGS. 6A and 6B are cross-sectional views, each illustrating a condition in which the living bodies are transferred to another container by pushing out the living bodies from the interior of the hole in the specific living body holding sheet with a pin.
Figure 6B:
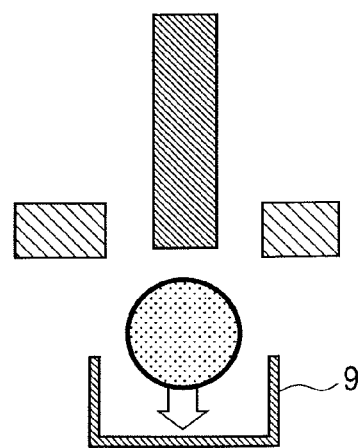

As specific examples, there can be used a method of directly pushing the living body with a rodlike pin 8, as illustrated in FIGS. 6A and 6B, or a method of using air pressure by spraying the living body with air 7, as illustrated in FIGS. 5A and 5B. In FIGS. 5A and 5B, the air 7 is sprayed from a nozzle 6. Further, water pressure can be used instead of air. A method using the air pressure is preferred in order to reduce the damage of the living bodies, and further, as illustrated in FIGS. 5B and 6B, a well that serves as a container 9 is arranged below the living body holding sheet, to thereby enable a specific living body to be simply transferred to a specific container at high speed. Hence, in this method, it is preferred that a process of transferring the living bodies from the holes include a process of spraying a hole selected as the hole including the living body to be transferred with air so as to blow away the living body to another container.

Another Use Example of Living Body Holding Sheet

Figure 7A:
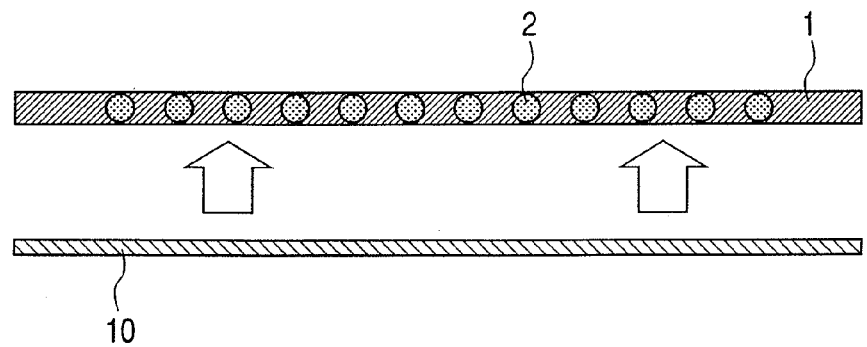
FIGS. 7A and 7B are diagrams illustrating a cross-sectional structure example illustrating the living body holding sheet with a bottom plate.
Figure 7B:

The living body holding sheet according to the present invention can be configured as a structure 26 in which after the living bodies are held and arranged within the holes, a flat plate 10 is brought in contact with the living body holding sheet and serves as a bottom plate thereof (FIGS. 7A and 7B). With the above-mentioned configuration, the living bodies can be more stably held, and, for example, a chemical material, such as a gene or protein peptide, can be implanted directly into the interior of the living bodies by using, for example, an introduction needle.

Applied Example Using Living Body Holding Sheet

The use of the living body holding sheet according to the present invention enables the living bodies per se to be observed, and an influence of the material that has been administered to the living bodies to be analyzed with a high throughput. In recent years, an attempt has been made to examine toxicity of the chemical material by using a fish embryo (in particular, Zebrafish). The living body holding sheet in accordance with the present invention can be used in such a case.

Further, the living body holding sheet according to the present invention is effective as a means for administering a specimen in question to the living bodies and analyzing the mutual action in the case of, for example, the activity of a medical agent, the screening of a medical agent, or the examination of water quality.

Processing Device

A processing device that processes living bodies by using the above-mentioned sheet that holds the living bodies includes holding means for holding the sheet and at least one means selected from the following means (A) to (G):

(A) means for arranging the living bodies in holes in the sheet;

(B) means for controlling a surrounding environment of the sheet to a given environment;

(C) supply means for supplying a liquid droplet to the holes in the sheet;

(D) observation means for observing a state of the living bodies that are held in the holes in the sheet;

(E) transfer means for transferring the living bodies that are held in the holes in the sheet from the sheet;

(F) recognition means for recognizing positions of the holes in the sheet; and (G) means for exchanging the liquid within the holes while keeping the living bodies in the holes in the sheet.

Figure 8:
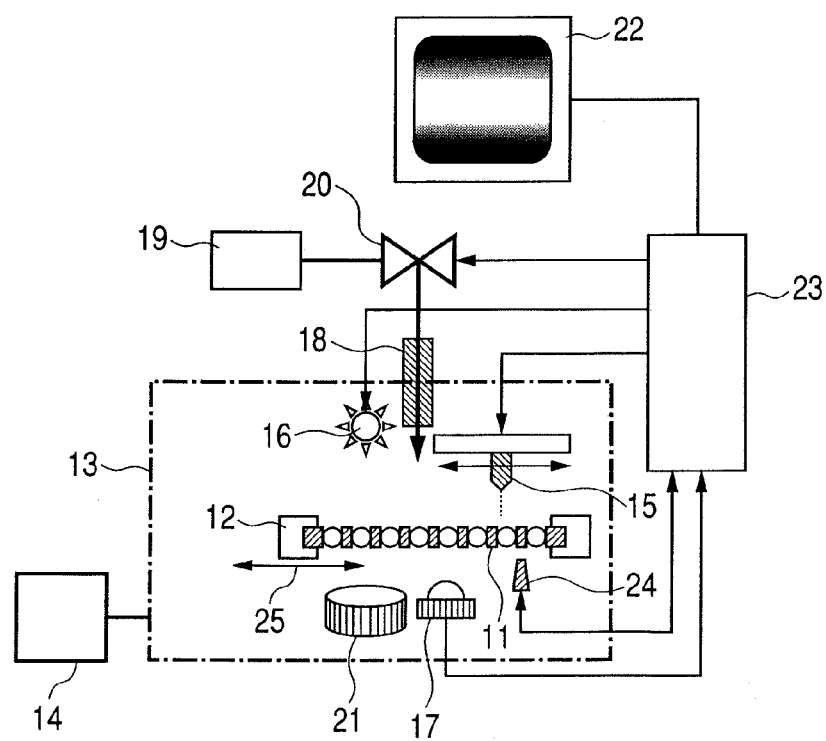
FIG. 8 is a schematic diagram illustrating a system configuration of a processing device that is used in the embodiment.
Figure 9A:
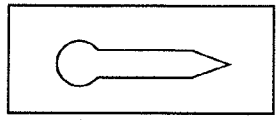
FIGS. 9A, 9B, 9C and 9D are diagrams illustrating examples of configurations of a juvenile fish living body holding sheet.
Figure 9B:
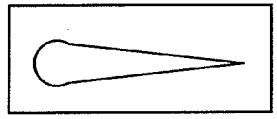
Figure 9C:
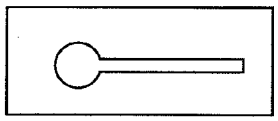
Figure 9D:
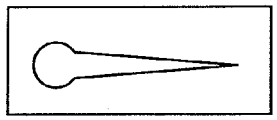

A system configuration example of a living body processing device using the living body holding sheet of the present invention is illustrated in FIG. 8. The operation of the device is described below. A living body holding sheet 11 that holds embryos of a large number of Zebrafish is fixed to a movable holder 12. The movable holder 12 makes the living body holding sheet movable in two axial directions X and Y. In this example, the Y-direction is indicative of a direction perpendicular to an X-direction 25 of FIG. 8 (direction perpendicular to the paper surface). The living body holding sheet is surrounded by a chamber 13 so as to be always maintained under a constant environment. The chamber 13 has the internal temperature and humidity controlled by a temperature/humidity control device 14 (device means (B)). In this embodiment, the temperature and the humidity are controlled to desired values to prevent the evaporation of moisture and to maintain the environment under which the embryos can grow. As a means for allowing the chemical material to affect the embryos, there is provided a liquid discharge device 15 (device means (C)) movable in a uniaxial direction (X-axis) from which a liquid droplet is discharged. The liquid discharge device is preferably a so-called ink jet discharge device, which can supply a desired liquid droplet of 1 to several tens picoliter on demand. The ink jet discharge device supplies a discharge energy to the liquid by means of an energy generating element, and discharges liquid droplets from a nozzle.

Figure 15:
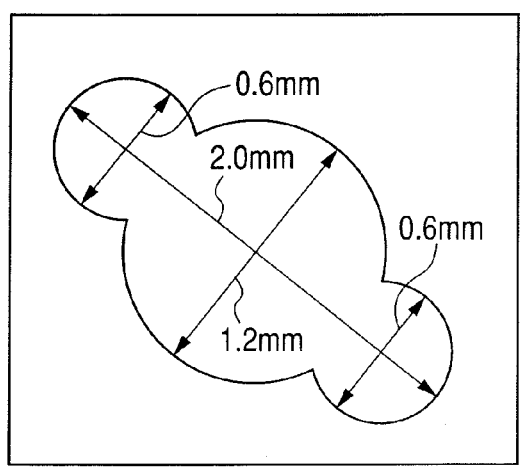
FIG. 15 is a diagram illustrating dimensions of a plane of a part of the living body holding sheet with the solution exchange portion.

In this embodiment, liquid including a chemical material, such as a cycloheximide solution (10 mg/ml), is supplied to the embryos. A given amount of liquid droplets are supplied to the respective embryos. In this situation, it is preferred that the chemical material with the same concentration be administered to three or more embryos with three or more kinds of different concentrations. Further, it is preferred that those embryos be made to grow together with an embryo to which no chemical material is supplied as a reference. Further, when the liquid exchange (cleaning) is completely conducted after the chemical material acts on the embryos, it is preferred to use the living body holding sheet having the liquid exchange portion of the dimensions illustrated in FIG. 15.

Figure 16:
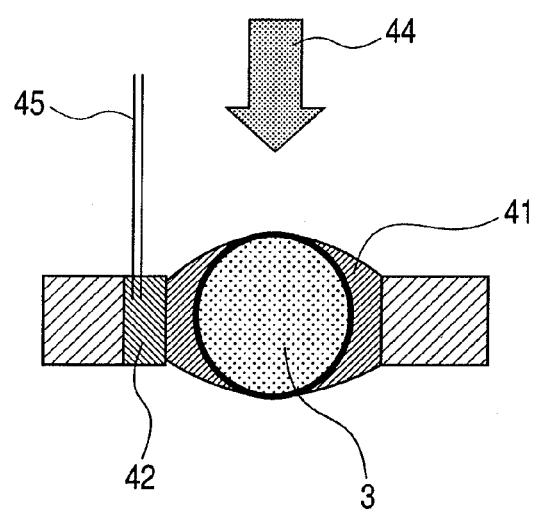
FIG. 16 is a cross-sectional view illustrating an example of a condition in which excess liquid is removed by bringing a capillary in contact with the liquid exchange portion.

Water drops on the liquid exchange portion so as to provide 100 nL with the aid of the liquid discharge device after a lapse of a given period of time from the supply of the chemical material to the embryos. At the same time, the excess liquid is removed by bringing a capillary 45 (0.68 mm in outer diameter and 0.20 mm in inner diameter) that is a liquid exchanging means in contact with the liquid exchange portion as illustrated in FIG. 16. The water is dropped in the direction of 44. The capillary 45 may be made of metal and glass and connected to pumping means that can suck or exhaust air within the capillary 45 or to a syringe. The above-mentioned operation is repeated multiple times to conduct the liquid exchange.

In the observation of the embryos, the bright field image is taken by a CCD camera 17 (device means (D)) that is disposed below the living body holding sheet while a visible light (white light: wavelength of 300 to 900 nm) is being applied from a lighting unit 16 to the embryos that are held by the living body holding sheet.

Further, the excitation light having a wavelength of 480 to 490 nm, which is spectroscopic, may be applied to the embryos from the lighting unit 16 to take a fluorescence image by the CCD camera. In this case, a fluorescent kind of living body staining material, such as acridine orange (5 mg/mL), is provided to the embryos by using the liquid discharge device 15 again for two hours, four hours, eight hours, and 16 hours with time after the chemical material has been supplied to the embryos, so that the embryos can be stained. Further, the visible image and the fluorescence image are taken after the living body holding sheet has been left at rest for a given period of time. The taken image is confirmed by a monitor 22 and then saved in a control unit 23. The control unit receives position information from a sensor unit 24 (device means (F)) that recognizes the hole positions of the living body holding sheet and controls the hole positions of the living body holding sheet through the movable holder 12.

Further, after 16 hours, air is sprayed to both the embryos that have been affected by the chemical material and the embryos that have not been affected by the chemical material from a gas spray nozzle 18 (device means (E)) through an electromagnetic valve 20 by a compressed air supply device 19, and the embryos can drop in respective collecting containers 21 having water therein, which are located at a lower portion. In that case, since the embryos are hatched after several days (about two days), juvenile fishes can be allowed to further grow. Further, a means for arranging the living bodies in holes in the sheet (Device means (A)) include a means using which the liquid having the living bodies in a slit coater or the like is brought in contact with the sheet (not shown in FIG. 8).

EXAMPLES

Examples of a holding sheet, a test method, and a processing device in the case of using embryos of Zebrafish and xenopus as living bodies are described below.

Example 1

Preparation of Living Body Holding Sheet

Polypropylene sheets of 100 mm square having diverse thicknesses were processed to prepare a living body holding sheet in the following manner.

Figure 4:
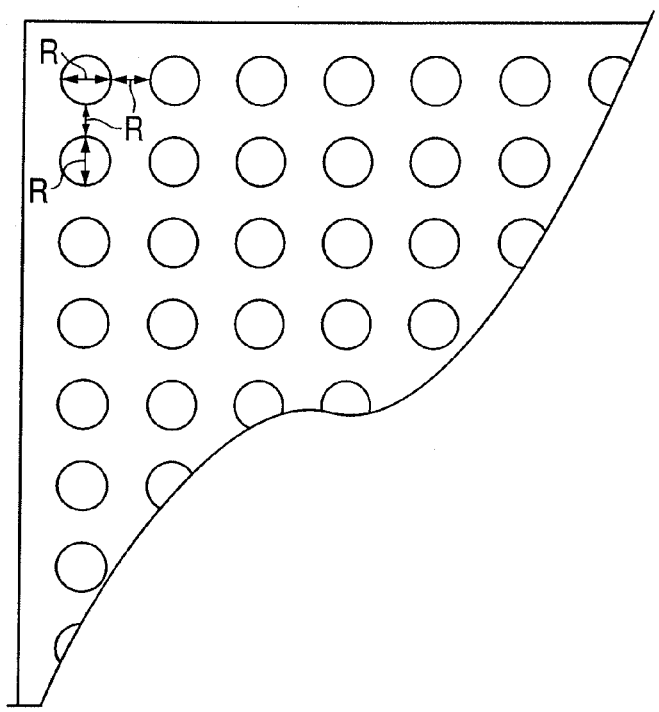
FIG. 4 is a plan view illustrating a living body holding sheet that is used in an embodiment.

The configuration of the holes was made so that 400 (20× 20) circular or square holes were arranged apart from adjacent holes by the same dimension as a hole diameter (R) at regular intervals as illustrated in FIG. 4.

The specification of the living body holding sheet that had been prepared for the purpose of holding and studying the embryos of Zebrafish that was about 1 mm in mean diameter is illustrated in Table 1 (hole configuration is circle (diameter D)).

Further, the specifications when the configuration of the holes is square (length of one side is L) are illustrated in Table 2.

The mean diameter of the embryos of the Zebrafish used as the living body in Tables 1 and 2 is about 1.0 mm. Accordingly, the thickness ratio (Th) illustrated in Tables 1 and 2 is calculated by t/1 when the thickness of the sheet is t mm. Further, the opening area ratio is calculated as the ratio (S1/S0) of an opening area S1 with respect to the maximum area S0 of the embryo.

Arrangement of Embryos

A water suspension 50 ml (20 embryos/ml) of the embryos of Zebrafish was poured on the living body holding sheet from above and brought into contact with the sheet. Thereafter, the excess liquid was removed from the sheet to hold the embryos in the respective holes in the sheet together with the liquid that existed in the holes. The excess liquid on the living body holding sheet is dropped by inclining the sheet so that water drops did not remain in places other than the opening portions.

Evaluation of Arrangement Efficiency

The respective opening portions (holes) of the living body holding sheet obtained in the above-mentioned manner in which the embryos were arranged were observed by a stereoscopic microscope to observe the holding state of the embryos in the respective holes.

The holes that hold only one embryo were counted up from 400 holes in the respective living body holding sheets. The count was made except for the holes in which the embryos were not held, or two or more embryos were held. Then, a rate of the holes into which one embryo was precisely inserted was calculated as the arrangement efficiency. Further, in Table 1, the efficiency evaluation of the embryo arrangement is illustrated in which the living body holding sheet that is equal to or higher than 90% in the arrangement efficiency is represented by ++, 70% to 80% is represented by +, 50% to 70% is represented by −, and 50% or lower is represented by −−.

TABLE 1

Living body holding sheet (hole configuration circle)

| No. | Hole configuration | Sheet thickness mm | Thickness ratio Th | Hole diameter mm | Opening area ratio S1/S0 | Embryo arrangement efficiency |
|---|---|---|---|---|---|---|
| 1 | circle | 0.8 | 0.8 | 0.9 | 0.81 | −− |
| 2 | circle | 0.8 | 0.8 | 1.0 | 1.00 | − |
| 3 | circle | 0.8 | 0.8 | 1.05 | 1.10 | + |
| 4 | circle | 0.8 | 0.8 | 1.1 | 1.20 | ++ |
| 5 | circle | 0.8 | 0.8 | 1.2 | 1.44 | ++ |
| 6 | circle | 0.8 | 0.8 | 1.3 | 1.69 | ++ |
| 7 | circle | 0.8 | 0.8 | 1.4 | 1.96 | ++ |
| 8 | circle | 0.8 | 0.8 | 1.5 | 2.25 | + |
| 9 | circle | 0.8 | 0.8 | 1.6 | 2.56 | + |
| 10 | circle | 0.8 | 0.8 | 1.7 | 2.89 | + |
| 11 | circle | 0.8 | 0.8 | 1.8 | 3.24 | + |
| 12 | circle | 0.8 | 0.8 | 1.9 | 3.61 | + |
| 13 | circle | 0.8 | 0.8 | 2.0 | 4.00 | − |

TABLE 1-continued

Living body holding sheet (hole configuration circle)

| No. | Hole configuration | Sheet thickness mm | Thickness ratio Th | Hole diameter mm | Opening area ratio S1/S0 | Embryo arrangement efficiency |
|---|---|---|---|---|---|---|
| 14 | circle | 0.8 | 0.8 | 2.1 | 4.41 | -- |
| 15 | circle | 0.1 | 0.1 | 1.2 | 1.44 | -- |
| 16 | circle | 0.2 | 0.2 | 1.2 | 1.44 | - |
| 17 | circle | 0.5 | 0.5 | 1.2 | 1.44 | ++ |
| 18 | circle | 0.7 | 0.7 | 1.2 | 1.44 | ++ |
| 19 | circle | 1.0 | 1.0 | 1.2 | 1.44 | ++ |
| 20 | circle | 1.5 | 1.5 | 1.2 | 1.44 | ++ |
| 21 | circle | 1.9 | 1.9 | 1.2 | 1.44 | + |
| 22 | circle | 2.0 | 2.0 | 1.2 | 1.44 | - |

TABLE 2

Living body holding sheet (hole configuration square)

| No. | Hole configuration | Sheet thickness mm | Thickness ratio Th | One-side length mm | Opening area ratio S1/S0 | Embryo arrangement efficiency |
|---|---|---|---|---|---|---|
| 23 | square | 0.8 | 0.8 | 0.9 | 1.03 | - |
| 24 | square | 0.8 | 0.8 | 1.2 | 1.83 | ++ |
| 25 | square | 0.8 | 0.8 | 1.8 | 4.13 | - |

Arrangement of Embryos of xenopus

A punching process was made for stainless sheets of 100 mm square having a thickness of 0.9 mm to prepare a living body holding sheet in the following manner.

The configuration of the holes was made so that 400 (20×20) circular holes were arranged apart from adjacent holes by the same dimension as the hole diameter (R) at regular intervals as illustrated in FIG. 4. The specification of the living body holding sheet that had been prepared for the purpose of holding and studying the embryos of the xenopus that was about 1.3 mm in mean diameter is illustrated in Table 3 (hole configuration is a circle with diameter D). A 50 ml (20 embryos/ml) water suspension of the embryos of xenopus was poured on the living body holding sheet from above and brought into contact with the sheet. Thereafter, the excess liquid was removed from the sheet to hold the embryos in the respective holes in the sheet together with the liquid that existed in the holes. The excess liquid on the living body holding sheet is removed by inclining the sheet so that water drops did not remain in places other than the opening portions.

The respective opening portions of the living body holding sheet obtained in the above-mentioned manner in which the embryos were arranged were observed by a stereoscopic microscope to observe the holding state of the embryos of the respective holes. The evaluation of the arrangement efficiency was made in the same manner as the evaluation method of the Zebrafish embryos, and illustrated together in Table 3.

TABLE 3

Xenopus embryo holding sheet (hole configuration circle)

| No. | Hole configuration | Sheet thickness mm | Thickness ratio (magnified) Th | Hole diameter mm | Opening area ratio S1/S0 | Embryo arrangement efficiency |
|---|---|---|---|---|---|---|
| 26 | circle | 0.9 | 0.7 | 1.2 | 0.85 | -- |
| 27 | circle | 0.9 | 0.8 | 1.35 | 1.08 | - |
| 28 | circle | 0.9 | 0.8 | 1.5 | 1.33 | ++ |
| 29 | circle | 0.9 | 0.8 | 1.8 | 1.92 | ++ |
| 30 | circle | 0.9 | 0.8 | 2.2 | 2.86 | - |
| 31 | circle | 0.9 | 0.8 | 2.6 | 4 | -- |

The observing method using the living body holding sheet according to the present invention is described in detail below. There was used a living body holding sheet (Table 1, No. 5) that held 20 Zebrafish embryos. The living body holding sheet was arranged within a chamber so as to be always maintained under a constant environment. The chamber had the internal temperature and humidity controlled. In this example, the temperature and the relative humidity were controlled to 28° C. and 85% RH, respectively, to prevent the evaporation of moisture, so that the environment is maintained under which the embryos can grow.

As a means for allowing the chemical material to affect the embryos, there was provided an ink jet device 15 that discharged a 4 pl liquid droplet. In this example, a given amount of liquid droplets were supplied to 12 embryos so that the total amount of cycloheximide solution (10 mg/ml) of each of the 3 embryos became 0.8 mL, 8 mL, 80 mL, and 800 mL, respectively. Together with three embryos to which no cycloheximide solution was supplied as a reference, 15 embryos in total were made to grow.

Figure 12A:
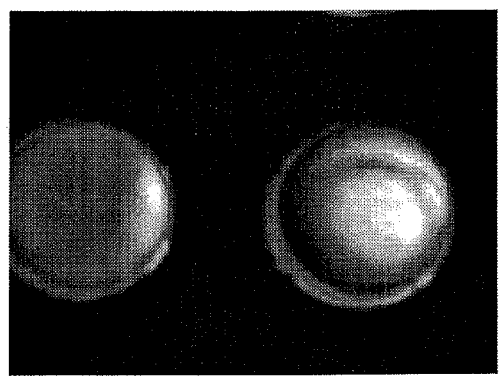
FIGS. 12A and 12B are photographs of the embryo, which is used in the embodiment.

In the observation of the embryos, the bright field image was taken by a CCD camera that was disposed below the living body holding sheet while a visible light (white light: wavelength of 300 nm to 900 nm) was being applied to the embryos that were held by the living body holding sheet. The bright field image that was taken four hours after the chemical material had been administered is illustrated in FIG. 12A. Further, the excitation light having a wavelength of 480 nm to 490 nm, which was spectroscopic, was applied to the embryos from a lighting unit 16 to take a fluorescence image by the CCD camera.

Figure 12B:
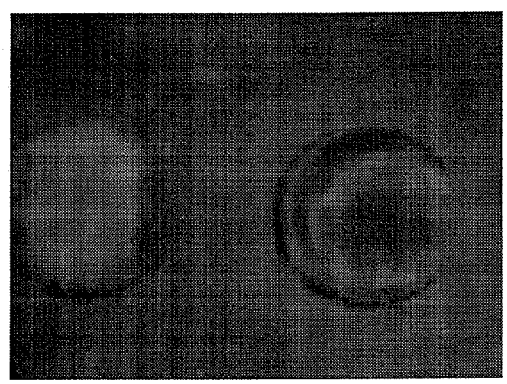

Acridine orange (5 mg/mL) was provided to the embryos by using the ink jet device 15 again for two hours, four hours, eight hours, and 16 hours with time after the chemical material had been supplied to the embryos, so as to provide the total amount of 1 nL. Then, the embryos were stained. Further, the visible image and the fluorescence image were taken after the living body holding sheet had been left at rest for 30 minutes. The fluorescence image obtained by staining the embryos four hours after the chemical material has been administered is illustrated in FIG. 12B.

Further, after 16 hours, air was sprayed from a commercially available gas spray nozzle to both the embryos that had been affected by the chemical material and the embryos that had not been affected by the chemical material, and the embryos dropped in respective collecting containers, which were located at a lower portion. In the container, containing water, the embryos were hatched two days after the dropping in, and juvenile fish were allowed to further grow.

Example 2

Growth Using Juvenile Fish Living Body Holding Sheet

In this example, after a fertilized embryo has been arranged on a living body holding sheet, growth and hatching are conducted, and juvenile fish can further grow five days or longer after hatching while the juvenile fish remain arranged.

Examples of the cross-sectional configurations of the holes in the living body holding sheet suitable for allowing the fertilized embryo of the Zebrafish immediately after embryo collection to grow five days or longer after hatch are illustrated in FIGS. 9A to 9D. The configuration can be made similar to the contour of the juvenile fish or the larva of amphibians. As the above-mentioned configuration, it is possible to preferably use the configuration having a head region that receives a head portion and a body region that receives a body portion and a tail portion. For example, it can have a simple oval configuration. Otherwise, the head region may have a circular configuration or a substantially circular configuration, and the body region may have a rectangular configuration, a triangular configuration, and the combination of a rectangle with a polygon, such as a triangle (FIGS. 9A to 9D). Further, it is preferred that the dimension of opening portion of the living body holding sheet in the direction of the long axis be in a range of from 1.1 times to 2 times of the body length of juvenile fish or larvae of amphibians. For example, in a case that a juvenile fish having a body length of about 4 mm is held, it is preferred that the dimension of opening area in the direction of the long axis be in a range of from 4.4 mm to 8 mm.

Figure 10:
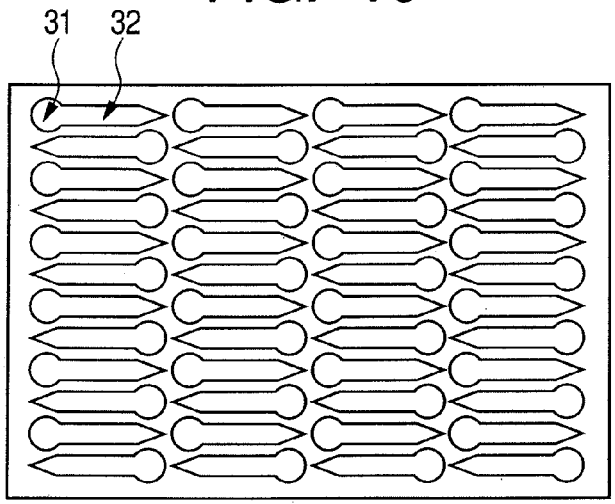
FIG. 10 is a plan view illustrating a juvenile fish living body holding sheet that is used in the embodiment.
Figure 11:
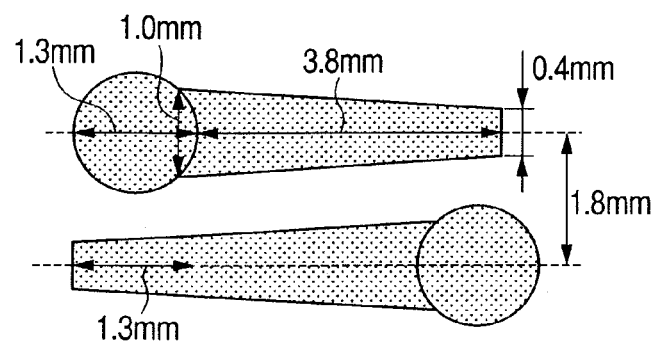
FIG. 11 is a diagram illustrating dimensions of a plane of a part of the juvenile fish living body holding sheet that is used in the embodiment.

As one example, a punching process was performed as illustrated in FIG. 10 so that a Teflon sheet having a size of 100 mm×150 mm with a thickness of 0.7 mm is configured so as to be similar to the contour of the juvenile fish having a body length of about 4 mm. Further, the configuration of the opening portion has an embryo holding area 31 and a growth area 32 that holds a growing portion of the juvenile fish (for example, body portion and tail portion) so that even the juvenile fish that has grown after hatching can further grow. Dimensions of the enlarged opening portion are illustrated in FIG. 11. The configuration illustrated in FIGS. 9A to 9D can be used as the configuration that can continuously accommodate the growth from the embryo to the juvenile fish.

Methylcellulose was added as a thickener to a suspension of the embryos of the Zebrafish 50 ml (20 embryos/ml) so that the concentration becomes 0.03 wt %. As the suspension, instant ocean (final concentration: 60 μg/mL) made by Aquarium Systems Corp was dissolved in distilled water. Further, penicillin of 5 unit/mL in the final and streptomycin of 5 μg/mL in the final were added as an antibacterial agent. The suspension of the fertilized embryo was poured on the living body holding sheet from above. Further, the excess liquid was removed from the sheet. The embryos were held in the respective embryo holding areas of the sheet together with the liquid that existed in the holes. The excess liquid on the living body holding sheet was removed by tilting the sheet so that the water drops did not remain in places other than the opening portions.

Figure 13A:
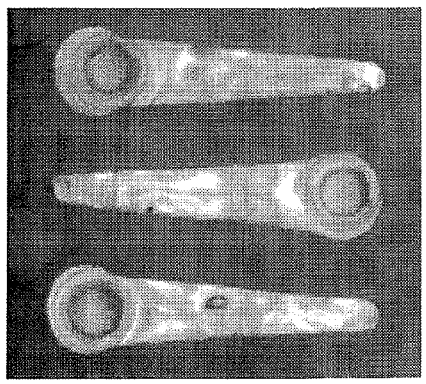
FIGS. 13A, 13B and 13C are photographs of the embryos and juvenile fish, which are used in the embodiment.
Figure 13B:
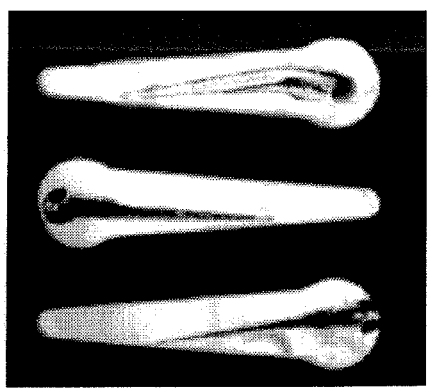
Figure 13C:
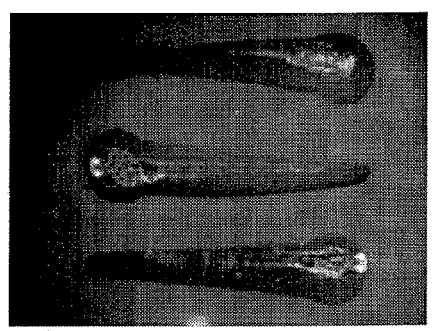

The living body holding sheet that held the embryos as in the above-mentioned manner was fitted to the above-mentioned processing device, and the bright field observation was conducted (FIG. 13A). Thereafter, the living body holding sheet was left as it was, and the embryos were hatched. During this time, for the purpose of compensating for the evaporation of water within the holes, water is appropriately discharged from the ink jet device. The bright field observation was again conducted three days after hatching. The bright field image is illustrated in FIG. 13B. Subsequently, a given number of liquid droplets are supplied to the juvenile fish to provide a 2-(4-(dimethylamino)styryl)-N-ethylpyridinium iodide (DASPEI) solution (38 mg/ml) of 5 nl in the final as the chemical material. The fluorescence image taken three hours after the liquid droplet has been supplied is illustrated in FIG. 13C.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2007-310946, filed Nov. 30, 2007, which is hereby incorporated by reference herein in its entirety.

The invention claimed is:

1. A method of holding living bodies, comprising:
   using a sheet in which multiple through-holes with a size capable of holding one of the living bodies but not capable of holding two or more of the living bodies are provided, to thereby arrange and hold the living bodies one by one in the multiple through-holes in the sheet together with a liquid such that the living bodies are not in direct contact with side walls of the through-holes; and
   transferring a selected living body from each of the multiple through-holes to a container,
   wherein the transferring comprises spraying with air a hole with the selected living body to blow the living body to the container, and
   wherein a thickness of the sheet in a vicinity of each of the multiple through-holes is from 0.2 times to 1.9 times of a maximum thickness of the living bodies held in the respective through-holes.

2. The method according to claim 1, wherein after the liquid having the living bodies is brought into contact with the sheet having the multiple through-holes, by removing excessive liquid from the sheet, one living body is held in each of the holes in the sheet together with the liquid that exists in the holes.

3. A test method using living bodies, comprising administering a material to each of the living bodies and examining a correlation with the material after the living bodies are held in the sheet by the method according to claim 1.

4. A growing method using multiple living bodies, comprising administering a material to each of the multiple living bodies to make the multiple living bodies grow within the through-holes in the sheet after the multiple living bodies are held by the method according to claim 1.

5. The method according to claim 4, wherein the proximity of the sheet that holds the multiple living bodies is controlled to a given environment.

6. The method according to claim 1, wherein each of the multiple living bodies comprises one of an individual in embryo, an individual after hatch, and an individual that has grown from the embryo.

7. The method according to claim 6, wherein the individual in embryo comprises one of an embryo of an amphibian and an embryo of a fish.

8. The method according to claim 3, wherein the administering the material comprises supplying a liquid droplet containing one of one kind of physiological active agent and multiple kinds of physiological active agents to the multiple through-holes in the sheet.

9. The method according to claim 8, wherein the liquid droplet is supplied by a discharging unit configured to a discharge liquid droplet of 100 pl (picoliter) or less.

10. The method according to claim 3, further comprising conducting liquid exchange after the administering the material.

11. The method according to claim 1, wherein the liquid within the multiple through-holes comprises at least any one of a moisturizing agent, a surface tension adjuster, and a thickener.

12. The method according to claim 1, further comprising introducing a light into the holes in the sheet for measurement or observation.

13. The method according to claim 1, wherein an opening area of each of the multiple through-holes is from 1.05 times to 3.61 times of a maximum cross-section of the living bodies.

14. The method according to claim 13, wherein each of the through-holes has a diameter that does not change in a thickness direction of the sheet.

* * * * *